United States Patent

Mitsui et al.

[11] 4,107,982
[45] Aug. 22, 1978

[54] VESSEL FOR ATMOSPHERE FOR USE WITH MATERIAL TESTING DEVICE

[75] Inventors: Murao Mitsui; Kiyoshi Yokogawa; Seiji Fukuyama, all of Kure, Japan

[73] Assignee: Agency of Industrial Science & Technology, Tokyo, Japan

[21] Appl. No.: 781,361

[22] Filed: Mar. 25, 1977

[30] Foreign Application Priority Data

Mar. 29, 1976 [JP] Japan .................. 51-34779

[51] Int. Cl.$^2$ .................................. G01N 3/08
[52] U.S. Cl. ................................... 73/95
[58] Field of Search ......................... 73/95, 15.6

[56] References Cited

U.S. PATENT DOCUMENTS

| 2,375,032 | 5/1945 | Parke et al. | 73/95 |
| 2,375,034 | 5/1945 | Semchyshen | 73/95 |

*Primary Examiner*—Anthony V. Ciarlante
*Attorney, Agent, or Firm*—Kurt Kelman

[57] ABSTRACT

A vessel for holding the atmosphere in which a test piece is tested has a test atmosphere chamber and an auxiliary chamber intercommunicably formed in a casing and a piston disposed freely slidably in the casing with the upper portion inside the auxiliary chamber and the lower portion protruding into the test atmosphere chamber. A test piece has one end thereof connected to the lower portion of the piston and the other end thereof fastened to a stay fixed in the test atmosphere chamber. A test gas is introduced under pressure into the test atmosphere chamber. The interior of the test atmosphere chamber and that of the auxiliary chamber are placed under an identical pressure. The surface areas of the piston are equal so that the strength of the test piece under a specific atmospheric condition can be accurately measured without subjecting the loading shaft to the otherwise possible effect of the pressure of the test atmosphere.

6 Claims, 6 Drawing Figures

VESSEL FOR ATMOSPHERE FOR USE WITH MATERIAL TESTING DEVICE

BACKGROUND OF THE INVENTION

This invention relates to a vessel for the atmosphere for use with a material testing device, which vessel enables the material testing device to measure the actual strength of a given test piece under a specific atmospheric condition.

Conventionally in a measurement of the strength of a given material under an atmosphere of high-pressure gas, for example, a test piece of the material is set in position within a vessel containing therein the atmosphere and measured for the strength. In this case, the magnitude of the force exerted by the test atmosphere is subtracted from the force externally measured and the difference thus found by the computation is regarded as representing the actual force applied to the test piece. In the case of the measurement of tensile strength, for example, a component of force of the high pressure gas which forms the test atmosphere acts in the direction of the axis of the test piece along which the tensile load is applied and what is actually measured in the circumstances is the nominal stress applied externally to the test piece plus the component of force, no matter whether the increased stress under the tensile load may result in decreased cross section, development of cracks or fracture of the test piece. For this reason, the actual stress in the most critical stage of the measurement from the time the application of load to the test piece is started through the time the test piece fractures under the load cannot be found by merely subtracting from the measured value the force in the direction of load which is invariably determined on the sole basis of the dimensions of the test piece and the shape of the vessel for holding the test piece.

An object of the present invention is to provide a vessel for the atmosphere for use with a material testing device, which vessel is characterized by venting the pressure of the atmosphere from affecting the applied stress during the measurement.

SUMMARY OF THE INVENTION

To accomplish the object described above according to the present invention, there is provided a vessel for the atmosphere for use with the material testing device, which vessel comprises a casing possessed of an auxiliary chamber in the upper portion and a test atmosphere chamber in the lower portion respectively through the medium of an airtight chamber, means for providing intercommunication between the test atmosphere chamber and the auxiliary chamber, a sliding member having the head portion thereof falling inside the auxiliary chamber and the bottom portion protruding airtightly into the test atmosphere chamber, means for equalizing the pressure to which the sliding member is exposed inside the auxiliary chamber and the pressure to which the sliding member is exposed inside the test atmosphere chamber, means disposed in the portion of the sliding member protruding into the test atmosphere chamber and adapted to support one end of the test piece, and a stay fastened inside the test atmosphere chamber and adapted to support the other end of the test piece, with the material testing device so disposed that one end of the shaft for applying the test load by the device is connected to the bottom of the casing and the other end of the shaft is pierced airtightly through the auxiliary chamber and connected to the head of the sliding member.

Because, as described above, the pressure inside the test atmosphere chamber and that inside the auxiliary chamber are equal and the surface area subject to the pressure within the former chamber and that within the latter chamber are also equal, it follows that the test piece will be supported under no load within the test atmosphere chamber and the pressure of the atmosphere has absolutely no effect upon the axial component of the load. Thus, the actual strength of the test piece under a specific atmospheric condition can be accurately measured.

The other objects and characteristic features of the present invention will become apparent from the description to be given in detail herein below with reference to the accompanying drawings.

DESCRIPTION OF THE PREFERRED EMBODIMENTS

Figure 1:
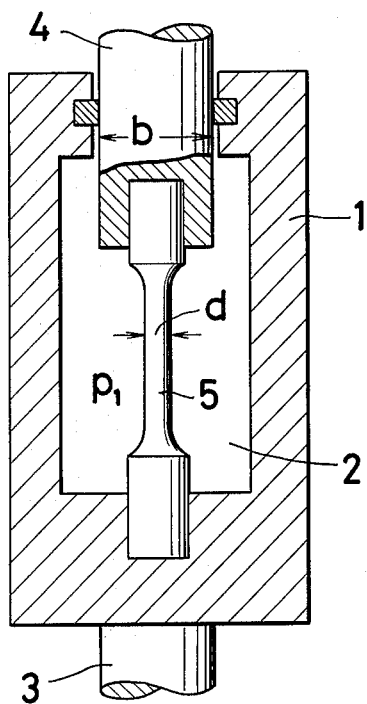
FIG. 1 is a cross section of the conventional vessel for the atmosphere for use with the material testing device.

The method for measuring the strength of a given material under a high-pressure atmosphere by use of the conventional vessel will be described with reference to FIG. 1. When the test atmosphere chamber 2 within the casing 1 is filled with a gas for the intended atmosphere under a pressure $p_1$, a force P represented by the following formula (1) is generated between the load shafts 3 and 4. This force P acts as a tensile force on the test piece 5.

$$P = [p_1 \times \pi/4 \, (b^2 - d^2)] \quad (1)$$

wherein, "b" stands for the diameter of the loading shaft 4 and "d" for the diameter of the portion of the test piece 5 under test.

It should be noted that as the material testing device applies stress to the test piece through the medium of the load shafts 3 and 4, the diameter "d" of the test piece is gradually decreased or the portion of the diameter partially sustains a crack, with the result that the surface area exposed to the pressure $p_1$ in the direction of the load shafts proportionally increases. Consequently, the force tending to push out the load shaft 4 gradually increases. When the test piece 5 is fractured in the final stage of the test, a great impulsive force represented by the formula (2) given below is exerted on the load shaft 4.

$$P = P_1 \times \pi/4 \, b^2 \quad (2)$$

This force is as high as 6,280 kg when, for example, the pressure $p_1$ within the atmosphere chamber 2 is fixed at 500 kg/cm$^2$ and the diameter of the load shaft 4 at 4 cm. With such a great force, there is a possibility that the load gauge, etc. disposed on the load shaft will sustain damage.

Figure 2:
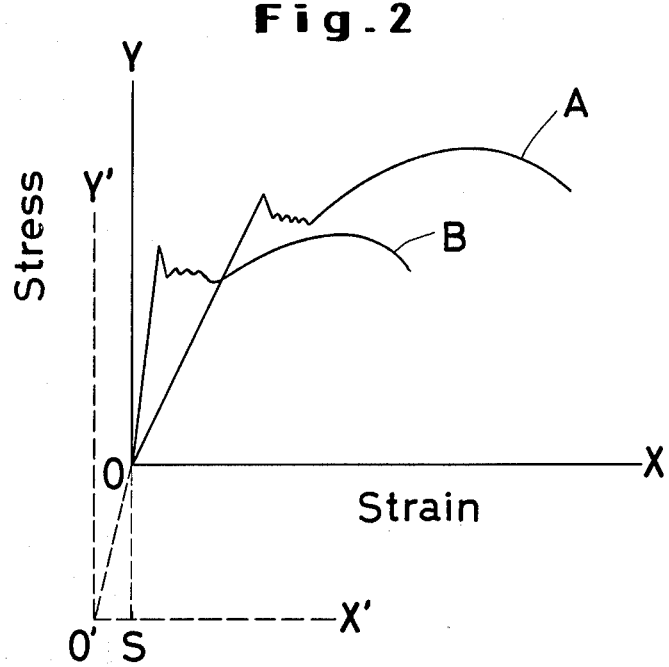
FIG. 2 is a graph showing the relation between the stress and strain as measured by use of the conventional vessel of FIG. 1.

Generally, the relation between the stress and strain between the time the application of load is started and the time the test piece fractures may be represented by a curve "A" of the X–Y coordinates in the case of a test performed on steel material under ordinary atmosphere or by a curve "B" of the X'–Y' coordinates in the case of a tensile test performed on steel material within a high-pressure vessel, as graphically shown in FIG. 2.

When the test piece is set in position within a high-pressure vessel, the test piece is exposed to the pressure by the high-pressure atmosphere while the pressure inside the high-pressure vessel is being increased to the prescribed test pressure. Because of the pressure, the test piece develops strain "S" as shown in the X'–Y' coordinates. Then the material testing device applies the load to the test piece which has already developed the strain "S". Hence the characteristic is represented by the curve "B" of the coordinates. The relation between the stress and strain actually determined by the material testing device is represented by only the solid line portion of the curve "B" in the zone of the X–Y coordinates, indicating that the actual stress by the pressure of the atmosphere cannot be accurately detected. Thus, while the yield strength of the material itself constituting the test piece ought to be invariable, both stress and strain are indicated to be smaller than they actually are. For the reason of the variation in the force tending to push out the load shaft owing to the phenomena of stretching, cracking and fracturing occurring in the test piece, the maximum strength and breaking strength of the test piece cannot be accurately computed by a mere correction effected by subtraction in the form of translational shift of coordinates. The curve "B", accordingly, assumes a deformed shape as compared with the curve "A". By the measurement described above, therefore, the actual value of the strength under the atmosphere of a specific condition cannot be obtained.

In view of the true state of affairs described above, the present inventors made various studies in search of a vessel for the atmosphere of a specific gas for use in the material testing device, which pressure vessel when used in the material test would not suffer the pressure of the atmosphere to have any effect on the measurement of the stress of load notwithstanding the change in the shape and dimensions of the test piece from the time of the beginning of the load application to the time of the fracture of the test piece. They have consequently accomplished the present invention. The vessel of the present invention for the atmosphere for use with the material testing device will now be described with reference to FIGS. 3 and 4.

Figure 4:
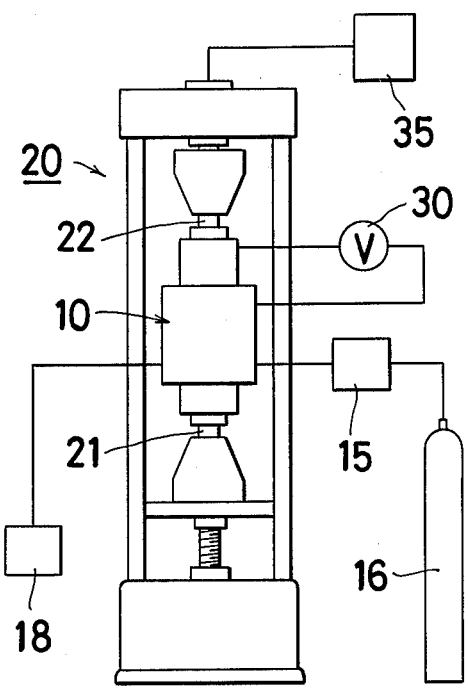
FIG. 4 is an explanatory diagram illustrating the condition in which the vessel of FIG. 3 is set in position in a material testing device.
Figure 3:
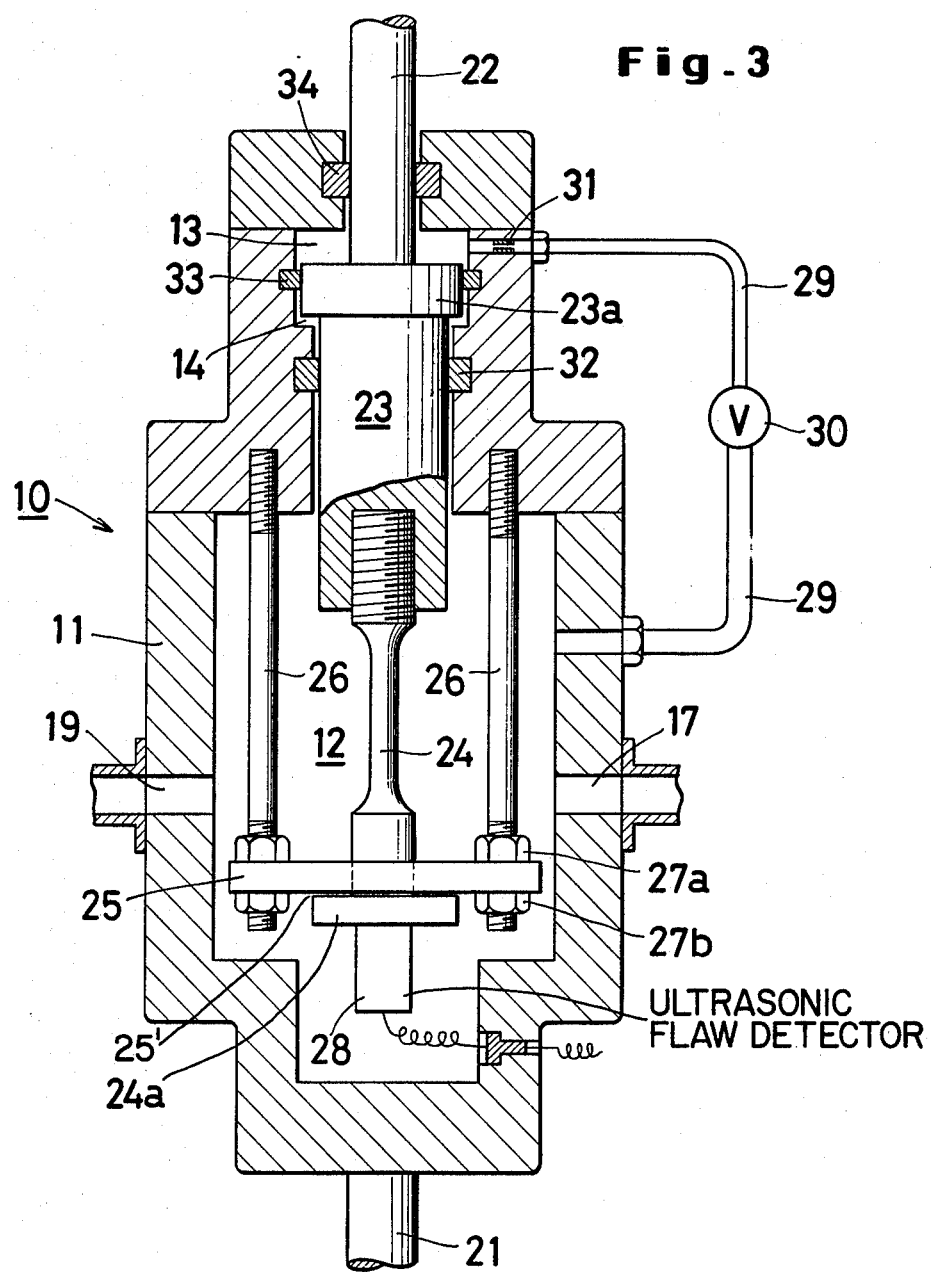
FIG. 3 is a cross section illustrating one embodiment of the vessel of the present invention for the atmosphere for use with the material testing device.

With reference to FIGS. 3 and 4, a casing 11 which forms the shell of the vessel 10 for the atmosphere for use with the material testing device incorporates therein a test atmosphere chamber 12 and on auxiliary chamber 13 disposed above the test atmosphere chamber and separated therefrom by an annular airtight chamber 14 formed of annular sealing members 32 and 33. The test atmosphere chamber 12 is provided with an inlet 17 connected through a high-pressure pump 15 to a gas source 16 for the test atmosphere and an outlet 19 connected to a vacuum pump 18.

Two load shafts 21, 22 which serve to apply the test load generated by the material testing device 20 to the test piece are disposed coaxially with each other. The load shaft 21 is kept in contact with the bottom portion of the casing 11 and the other load shaft 22 is pierced through the upper side of the casing so that the lower end thereof is coaxially connected inside the auxiliary chamber with a flange 23a of a piston-like sliding member 23 whose lower end protrudes into the test atmosphere chamber and whose upper end is topped by the flange 23a. The load shaft 22, the flange 23a and the sliding member 23 are in airtight contact with the inner wall of the casing 11 through the medium of annular sealing members 32, 33 and 34. The casing 11, in the embodiment illustrated in FIG. 3, is composed of three component members. It may otherwise be composed of only two component members or of four or more component members insofar as the component members are connected with perfect airtightness.

The test piece which is supported inside the test atmosphere chamber 12 is connected at its upper end to the lower end of the sliding member 23. Screw threading, bayonet mounting or other similar means may be used for the union of the test piece with the sliding member. An engaging head 24a which is formed at the lower end of the test piece 24 is held in engagement with a stay 25 which is fastened in position with nuts 27a, 27b to the leading ends of a plurality of supporting rods 26 fixed to the upper portion of the test atmosphere chamber so as to leave gap 25' between test piece engaging head 24a and stay 25. This means that the engaging head 24a of the test piece 24 is disposed in a space to which the gas forming the atmosphere within the test atmosphere chamber can freely flow and is restrained in the tensile direction by the stay 25. Denoted by 35 is a detector for the test device 20.

As occasion demands, the engaging head 24a of the test piece may be provided with an ultrasonic flaw detector 28 capable of monitoring the behavior such as of cracks sustained by the test piece during the application of test load.

The auxiliary chamber 13 serves the purpose of permitting the pressure of the gas filling the test atmosphere chamber 12 to bear on the surface of the sliding member 23 falling inside the auxiliary chamber so as to offset the force issuing from the pressure and tending to push the sliding member out of the test atmosphere chamber. A pipe 29 constitutes a compressed fluid path through which the test atmosphere chamber 12 and the auxiliary chamber 13 are allowed to communicate with each other and are held under an equal pressure. An orifice 31 is disposed where the pipe 29 reaches the auxiliary chamber 13.

The flange 23a formed on the sliding member 23 is intended to equalize the surface area on which the pressure is exerted inside the test atmosphere chamber 12 upon the sliding member and the surface area on which the pressure is similarly exerted inside the auxiliary chamber 13. To be more specific, the surface area on which the pressure is exerted inside the auxiliary chamber, namely the area of the end surface of the flange 23a excluding the portion occupied by the load shaft 22 and the area of the lower surface of the sliding member 23 exposed to the pressure inside the test atmosphere chamber are made equal. If, in this case, the sliding member and the test piece are in airtight contact with each other, then the area to be thus equalized is the annular portion which remains after exclusion of the portion of the lower surface of the sliding member occupied by the test piece. If the sliding member supports the test piece loosely, then the area to be equalized is the entire area of the lower surface of the sliding member. In the event that the surface area exposed to the pressure inside the auxiliary chamber 13 and that inside the test atmosphere chamber 12 cannot be equalized, the force exerted on the sliding member from the test atmosphere chamber side and that exerted similarly from the auxiliary chamber side can be equalized by incorporating in the fluid path 29 a pressure regulating valve 30 and properly controlling the pressure reaching the interior of the auxiliary chamber 13 through the adjustment of the valve 30.

Examples of the gases which are usable as fluids to fill the space within the test atmosphere chamber generally include air, hydrogen and argon. Liquids such as water and oil may likewise be used. The atmosphere may be held at elevated temperatures and lowered temperatures as well as at room temperatures.

In the vessel of the present invention having the foregoing construction and serving to hold the atmosphere for use with the material testing device, first the test piece 24 is mounted between the sliding member 23 and the stay 25 inside the test atmosphere chamber 12. A gap 25' of about 1 mm given in the axial direction between the stay 25 and the engaging head 24a of the test piece serves to facilitate this mounting of the test piece.

Then, the fluid for the test atmosphere is fed from the fluid source 16 via a high-pressure pump 15 to the test atmosphere chamber 12 until the pressure of the fluid inside the test atmospheric chamber rises to the predetermined test pressure. In this case, the valve 30 is left open, so that the fluid is forwarded via the pipe 29 to the auxiliary chamber 13, with the result that the force acting upon the sliding member 23 from the test atmosphere chamber side and the force acting similarly from the auxiliary chamber side become equal. Thus, the stress exerted on the test piece because of the pressure generated inside the test atmosphere chamber 12 can be cancelled. Up to the time that the material test is started, the test piece 24 is maintained in a state free from applied load. The two load shafts 21 and 22 of the material testing device 20 are first moved in opposite directions until the space intervening between the stay 25 and the engaging head 24a of the test piece 24 is completely eliminated. The frictional force generated between the load shaft 22 and the sealing members 32, 33 and 34 by the movement of the load shafts is detected by the load cell (not shown) of the material testing device. After the stay and the engaging head 24a have come into intimate contact, the two load shafts are further moved to commence the tensile test. Even if the test piece sustains the constriction, stretching, crack, growth or fracture in the course of the test, since controlled back pressure is caused to act upon the sliding member within the auxiliary chamber 13, only the test load that is given by the material testing device is exerted on the test piece. Inside the test atmosphere chamber, therefore, the test piece is not at all subject to any effect of the pressure of the gas forming the atmosphere in the chamber.

Further, the impulsive force which acts upon the sliding member at the time that the test piece is broken under the load can be alleviated by means of the orifice 31. If the test piece 24 is provided with the ultrasonic flaw detector 28, then the condition of crack developing in the test piece can be monitored at all moments along the course of test. Moreover, the development of the test itself can be kept under observation by virtue of the formation of cracks taken in conjunction with the elongation of the test piece. The actual strength of the test piece under a specific atmosphere can accurately be found by subtracting from the measured value the value previously found in the absence of the load.

In the event that the surface area on which the pressure is received within the auxiliary chamber 13 and that within the test atmosphere chamber 12 are not equal, the same results as those obtainable where said pressures are equal can be obtained by adjusting the pressure control valve 30 incorporated in the fluid path 29 in such a way that the ratio of pressures of the fluid produced in the two chambers is in reverse proportion to the ratio of the surface areas exposed to the fluid pressure respectively in the chambers.

The vacuum pump 18 which is connected to the test atmosphere chamber 12 is used for the purpose of displacing the gas filling the test atmosphere chamber with a separate specific gas or evacuating the test atmosphere chamber to permit a test under vacuum.

One example of a test conducted with a material testing device employing the vessel for atmosphere of this invention will now be described.

Figure 5:
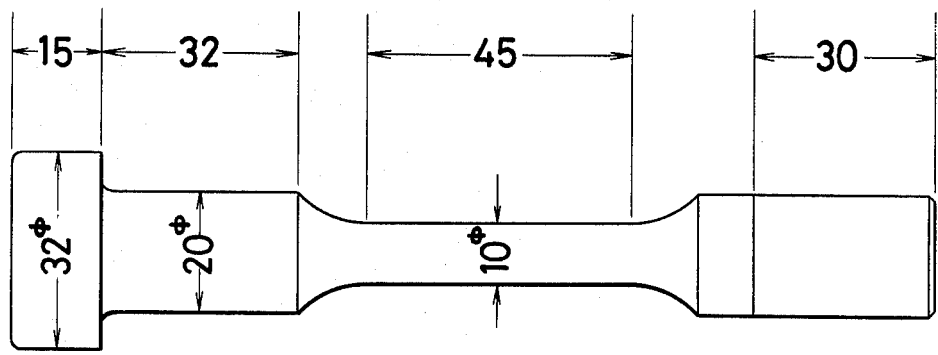
FIG. 5 is a front view illustrating the test piece used in the present invention.

A tensile test was performed on carbon steel 1015 (SAE) having the dimensions shown in FIG. 5 under normal room temperature by setting the test piece in position within the pressure vessel shown in FIG. 3 so as to leave a 0.8 mm space between the engaging head of the test piece and the stay and introducing argon gas into the vessel so that both the test atmosphere chamber and the auxiliary chamber were under pressure of 100 Kg/cm$^2$. The results detected by the load cell of the material testing device were as shown in FIG. 6.

Figure 6:
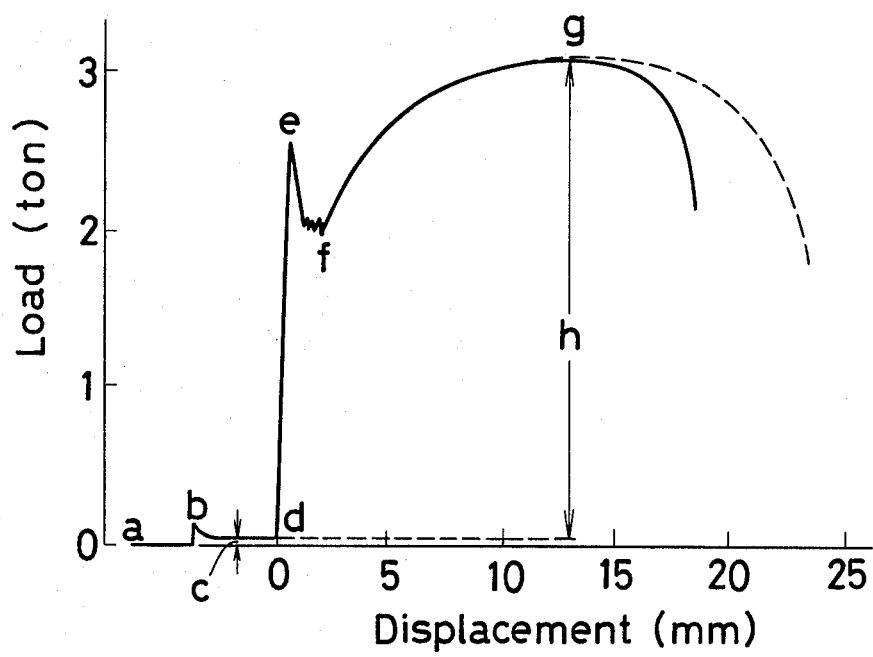
FIG. 6 is a graph showing the relation between the load and dispersement as measured by use of the vessel according to the present invention.

With reference to FIG. 6, the graph shows the relation between the load applied by the loading shaft (longitudinal axis) and the displacement of the test piece (transverse axis). Argon gas was introduced into the test atmosphere chamber between the point "a" and the point "b". A load was applied to the test piece via the loading shaft at the point "b" and substantially no load was applied to the test piece between the point "b" and the point "d". Therefore, the frictional force between the loading shaft and the sealing members is shown by "c". At the point "d", the test piece was brought into close contact with the stay and a load was applied thereto by the loading shaft. The test piece was deformed slightly as the stress thereon was increased to about 2.6 tons. As soon as the test piece reached its upper yield point (the point "e"), the displacement (stretch) thereof increased suddenly and the stress thereon decreased to about 2 tons. As soon as the test piece reached its lower yield point (the point "f"), the stretch and stress of the test piece increased, the stress thereof maintained a saturated state (the portion "g") for a while and thereafter the test piece was fractured upon stretching to about 18 mm. Accordingly, the actual value of the maximum stress of the test piece is shown by "h", and the stress of the test piece can be exactly and easily calculated. Further, the chain line in FIG. 6 shows the case where a tensile test was performed in the same manner as described above except that hydrogen instead of the argon gas was used.

As is clear from the above description, the vessel for atmosphere according to the present invention has a test atmosphere chamber and an auxiliary chamber provided in communication with each other. A material to be tested is held in the test chamber so as to have one of its ends in unrestricted contact with the test atmosphere and so as to leave a slight gap between said end and the stay which holds it. By adjusting the pressure of the atmosphere in the auxiliary chamber so that it exerts a force on the sliding member which is equal and opposite that exerted on the sliding member by the atmosphere in the test atmosphere chamber, the test piece can be held in the test atmosphere chamber in a load-free state. Furthermore, since the test can be conducted with complete freedom from any change in the effect of test atmosphere pressure which would otherwise result at the time of necking, stretching or cracking of the test piece and since the frictional force acting on the load shaft is also simultaneously measured and taken into consideration, the strength of the material can be accurately measured during all critical test periods between the start of the test and fracture of the test piece.

What is claimed is:

1. A vessel for retaining an atmosphere in which a test piece is tested, comprising in combination:
    (a) a casing defining an auxiliary chamber in an upper portion and a test atmosphere chamber in a lower portion, the auxiliary chamber and the test atmosphere chamber being separated by an airtight chamber,
    (b) means for providing intercommunication between said test atmosphere chamber and said auxiliary chamber,
    (c) a sliding member having a head portion thereof inside the auxiliary chamber and a bottom portion protruding airtightly into said test atmosphere chamber,
    (d) means for equalizing the pressure to which the sliding member is exposed inside the auxiliary chamber and the pressure to which said sliding member is exposed inside the test atmosphere chamber,
    (e) means disposed in the portion of said sliding member protruding into the test atmosphere chamber and adapted to support one end of the test piece,
    (f) a stay fastened inside the test atmosphere chamber and adapted to support the other end of said test piece, and
    (g) a shaft for applying a test load to the test piece, one end of the shaft being connected to the bottom of said casing and the other end of said shaft passing airtightly through the auxiliary chamber and connected to the head portion of said sliding member.

2. The vessel according to claim 1, wherein the surface areas of the sliding member exposed to pressure in the auxiliary chamber and in the test atmosphere chambers are equal, and the means for equalizing said pressures is a pipe connecting the auxiliary and test atmosphere chambers.

3. The vessel according to claim 1, wherein the means for equalizing the pressure to which the sliding member is exposed within the test atmosphere chamber and that within the auxiliary chamber comprises a pressure control valve incorporated in the fluid path, which valve permits pressure adjustment such that the ratio of pressures of the atmosphere in the two chambers is in reverse proportion to the ratio of the surface areas exposed to the fluid pressure respectively in the chambers.

4. The vessel according to claim 1, wherein the test piece and the stay are fixed so as to define a gap therebetween.

5. The vessel according to claim 1, further comprising an ultrasonic flaw detector in said test atmosphere chamber.

6. The vessel according to claim 1, further comprising an orifice in said means for providing intercommunication between the test atmosphere chamber and the auxiliary chamber.

* * * * *